(12) United States Patent
Blum et al.

(10) Patent No.: US 6,702,794 B2
(45) Date of Patent: Mar. 9, 2004

(54) OSTOMY POUCH CLAMP

(75) Inventors: John L. Blum, Toms River, NJ (US); John B. Cline, New Brunswick, NJ (US); Kathryn A. Gargiulo, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 163 days.

(21) Appl. No.: 10/128,613

(22) Filed: Apr. 23, 2002

(65) Prior Publication Data

US 2003/0198704 A1 Oct. 23, 2003

(51) Int. Cl.⁷ .................................................. A61F 5/44
(52) U.S. Cl. ..................... 604/335; 24/30.5 R; 604/277
(58) Field of Search ................................ 604/277, 327, 604/332–345, 355; 383/78; 24/30.5 R, 30.5 W, 30.5 P, 30.5 T, 30.5 S, 30.5 L

(56) References Cited

U.S. PATENT DOCUMENTS

| 3,266,711 | A | * | 8/1966 | Song .............................. 383/13 |
| 3,523,534 | A |   | 8/1970 | Nolan et al. |
| 3,629,905 | A | * | 12/1971 | Cote ........................... 24/30.5 R |
| 4,390,019 | A |   | 6/1983 | Leveen et al. |
| 4,403,991 | A |   | 9/1983 | Hill |
| 4,460,359 | A |   | 7/1984 | Fenton |
| 4,465,486 | A |   | 8/1984 | Hill |
| 4,523,353 | A | * | 6/1985 | Hubbard et al. ......... 24/30.5 R |
| 4,551,888 | A |   | 11/1985 | Beecher |
| 4,887,335 | A | * | 12/1989 | Folkmar ................... 24/30.5 R |
| 4,983,172 | A |   | 1/1991 | Steer et al. |
| 5,050,272 | A | * | 9/1991 | Robinson et al. ........ 24/30.5 R |
| 5,125,133 | A |   | 6/1992 | Morrison |
| 5,379,489 | A |   | 1/1995 | Delk et al. |
| 5,598,608 | A | * | 2/1997 | Naslund ................... 24/30.5 R |
| 5,604,959 | A | * | 2/1997 | Bowen ..................... 24/30.5 R |
| 5,617,616 | A |   | 4/1997 | Cutts, Sr. |
| 5,619,775 | A |   | 4/1997 | Klinck |
| 5,713,108 | A | * | 2/1998 | Solomon et al. ......... 24/30.5 R |
| 5,735,022 | A | * | 4/1998 | Niedecker ................ 24/30.5 R |
| 5,968,023 | A | * | 10/1999 | Olsen ......................... 604/334 |
| 6,058,572 | A | * | 5/2000 | Folkmar ................... 24/30.5 R |
| 2002/0010444 | A1 | * | 1/2002 | Wiltshire et al. ........... 604/335 |
| 2002/0133916 | A1 | * | 9/2002 | Folkmar ................... 24/30.5 R |

FOREIGN PATENT DOCUMENTS

| EP | 0153044 |   | 8/1985 |   |
| GB | 2243789 |   | 11/1991 |   |
| GB | 2 346 328 A | * | 9/2000 | .......... A61F/5/445 |
| WO | WO 92/03353 | * | 3/1992 | .......... B65D/77/12 |
| WO | WO 93/16930 | * | 9/1993 | .......... B65D/33/16 |

* cited by examiner

Primary Examiner—Weilun Lo
Assistant Examiner—Michael Bogart
(74) Attorney, Agent, or Firm—Stuart E. Krieger

(57) ABSTRACT

An ostomy pouch clamp/closure and a method of production are described. The clamp comprises a blade member and a trough member hingedly coupled to the blade member and having a blade member receiving channel. At least one of the members comprises integrally molded first and second portions, being respectively a rigid portion of a first relatively hard plastics, and a soft or comfortable-feel portion of a second relatively deformable plastics. The clamp can be formed using two-shot molding. The channel also includes an elongate constriction for releasably retaining the blade member in the channel, providing a mechanical interlock along the entire length of the clamp. The clamp also includes a snap lock at its distal end.

18 Claims, 4 Drawing Sheets

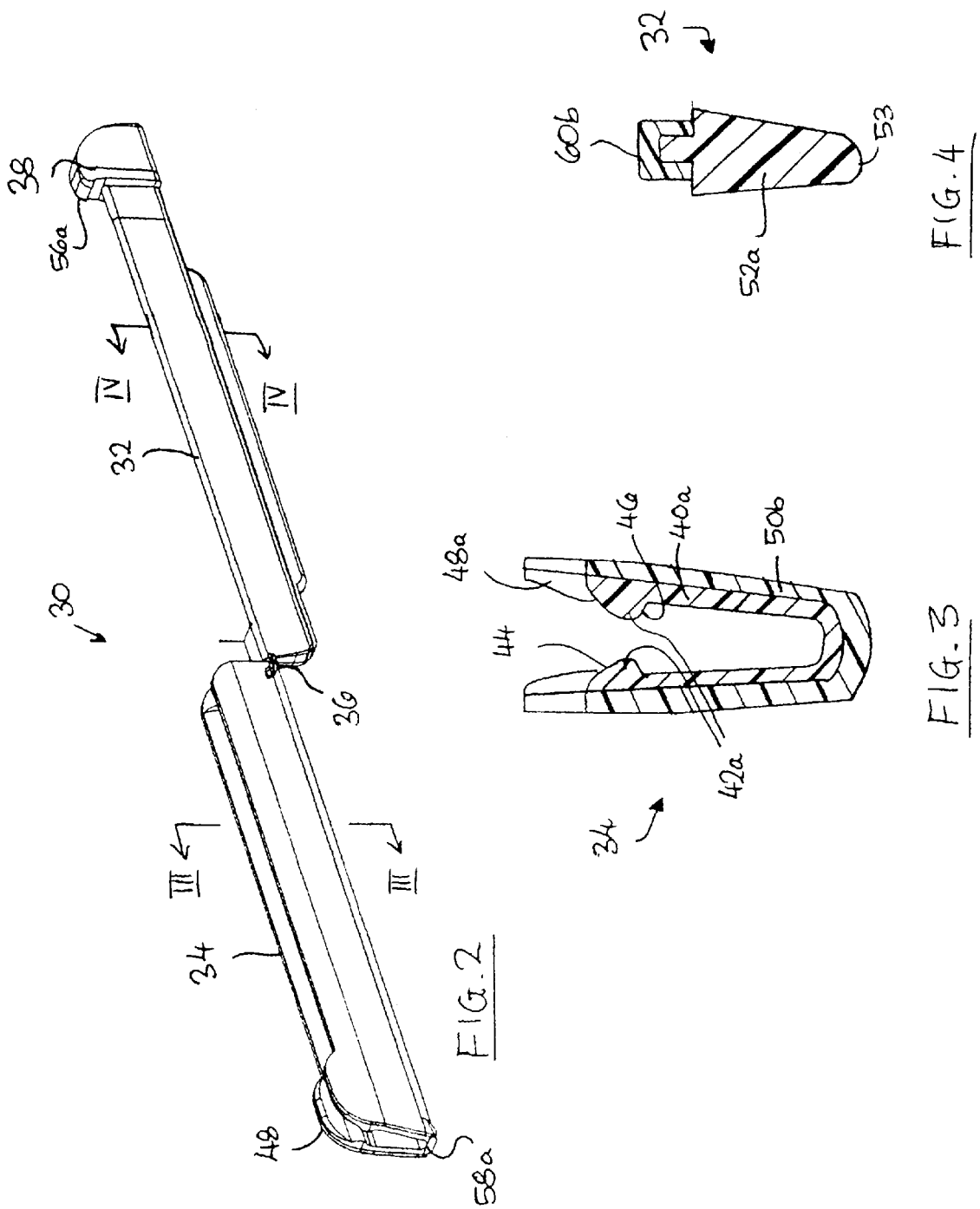

OSTOMY POUCH CLAMP

FIELD OF THE INVENTION

The present invention relates to a clamp or closure for closing an open end of a drainable ostomy pouch. The invention is especially suitable for an integrally molded one-piece plastics clamp, but it is not limited exclusively to this.

BACKGROUND TO THE INVENTION

An example of a conventional one-piece molded plastics clamp is described in U.S. Pat. No. 5,125,133, and is also shown in appended FIG. 1. The clamp consists of a thin wedge or blade member 10 receivable in the channel 12 of a narrow trough member 14 for clamping the outlet end of an ostomy pouch. One end of the blade member is hinged to a corresponding end of the trough member by an integral flexible hinge strap 16. The other end of the blade member is formed with a deformable cantilever lock 18 for forming a snap fit engagement with a lock keep 20 on the rough member.

The clamp is necessarily made of a relatively stiff, only slightly deformable plastics for optimum structural rigidity. Structural rigidity is important to ensure a tight clamping action, in order to prevent leakage of the pouch contents past the clamp. Such leakage would be highly embarrassing and unhygienic for the wearer. The comfort of the user is a secondary consideration in the above design. Also, in the above design of clamp, the blade member 10 and the trough member 14 are only coupled together at their ends. Since the clamp could be vulnerable to breakage or damage of the hinge strap 16, an additional guide 22 has to be provided on the blade member 10 at its end to prevent the blade member from falling out of the channel 12 were the hinge strap 16 accidentally to be broken in use.

Reference may also be made to U.S. Pat. No. 4,983,172, which describes another example of a one-piece clamp. This clamp is held in its closed position by means of lips located at the distal end of the channel or trough member, which snap over the top of the blade member when the blade member is pivoted to its closed position. The distal end of the blade member projects from the channel, and finger tabs are provide adjacent to the lips for applying pressure to open the clamp.

SUMMARY OF THE INVENTION

Broadly speaking, one aspect of the invention is to form at least one of the trough member and the blade member from integrally molded first and second plastics. The first plastics is relatively hard, and forms a first portion of the blade member and/or trough member. The second plastics is relatively deformable or soft, and forms a second portion of the blade member and/or trough member.

The first plastics can therefore provide structural rigidity for the clamp, to ensure reliable clamping action to avoid leakage of pouch contents. The second plastics can provide a soft or cushioned surface, to give the clamp a more comfortable feel to the user. This can improve user acceptance, and make the clamp more comfortable to wear.

In one form, both the blade member and the trough member include respective portions made of the first and second plastics material.

In another aspect, the invention relates to a method of integrally molding such a clamp with respective first and second portions of first and second plastics.

Another broad aspect of the invention is for the blade member and the trough member to be configured with inter-engaging profiles for forming an elongate mechanical interlock substantially along the channel of the trough member. In one form, the mechanical interlock is provided by an elongate constriction in the channel near to its mouth. This feature can also be used to create a seal between the layers of the pouch.

Another broad aspect of the invention is for the blade member to comprise a locking projection towards its distal end, for locking engagement with a portion of the trough member towards its distal end. The portion of the trough member may be located adjacent to the bottom (or floor) of the channel of the trough member. Therefore, instead of engaging only with a portion near the top or mouth of the channel as in the prior art, the locking projection can engage with a portion adjacent to the bottom of the channel.

The above aspects may be used independently, or advantageously in combination.

Advantages of the invention in its various aspects include: a softer exterior feel for the user, making the clamp more comfortable to wear; a more positive clamping action along the length of the clamp; and an alternative unlocking technique to the cantilever lock of the prior art. These and other features and advantages of the invention will become more apparent from the following description of a non-limiting embodiment of the invention.

BRIEF DESCRIPTION OF THE DRAWINGS

FIG. 2 is a schematic perspective view of an embodiment of the invention, shown in its open position;

FIG. 3 is an enlarged schematic section along the line III—III of FIG. 2;

FIG. 4 is an enlarged schematic section along the line IV—IV of FIG. 2 (shown inverted to match the orientation of the profile in FIG. 3);

DETAILED DESCRIPTION OF PREFERRED EMBODIMENT

Figure 6:
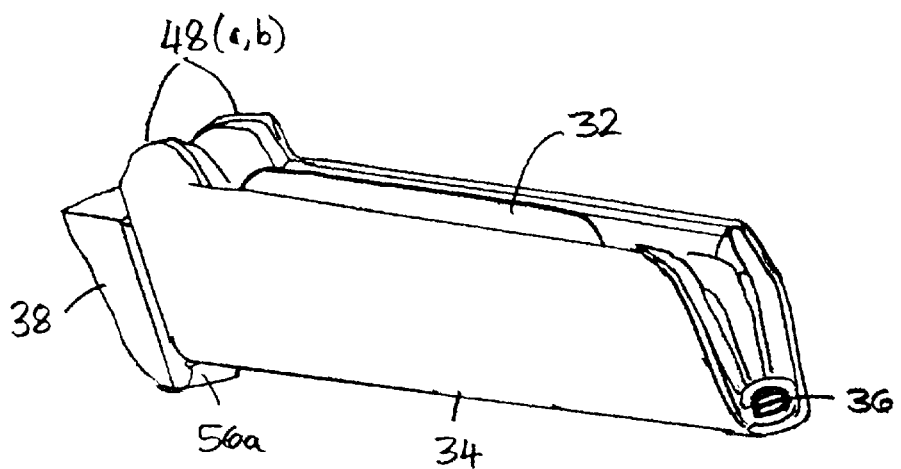
FIG. 6 is a schematic rear perspective view showing the clamp in its closed position.
Figure 7:
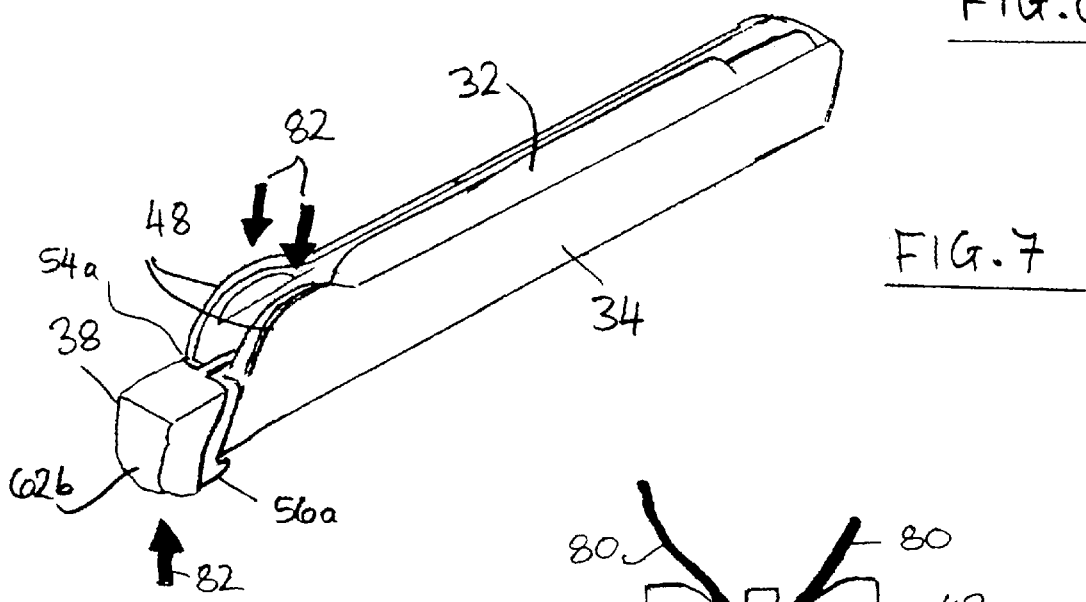
FIG. 7 is a schematic front perspective view showing the clamp in its closed position.

FIG. 2 shows a one piece ostomy pouch clamp 30 of molded plastics. The clamp 30 includes a blade member 32 integrally joined to a trough member 34 by a flexible hinge strap 36. The blade member 32 is dimensioned to be receivable within the channel of the trough member 34 when the blade member 32 is moved to its closed position (as shown in FIGS. 6 and 7). The distal end of the blade member 32 is formed with an enlarged handle portion 38 which projects longitudinally of the trough member 34 when in the closed position.

An important feature of this embodiment is that at least one of the blade member 32 and the trough member 34 consists of a first portion of a first plastics and a second portion of a second plastics, integrally molded to form a one-piece device. In the present embodiment, both the blade member 32 and the trough member 34 are constructed in this manner. In the following, the suffix "a" is used with reference numerals to identify portions molded of the first plastics, and the suffix "b" is used to identify portions molded of the second plastics. The first plastics is a relatively hard or rigid plastics, to provide the necessary structural rigidity. Examples of the first plastics include polypropylene, high density polyethylene, nylon and filled styrene acrylonitrile (SAN). The second plastics is a relatively soft, deformable plastics, to provide a soft or cushioned feel to the user. Examples of the second material include thermoplastic elastomers, thermoplastic olefins, thermoplastic urethanes, polyvinyl chloride, natural rubber, and silicone rubber. As used herein, the terms relatively soft and relatively hard refer to each other, so that one plastics is harder than the other.

Figure 5:
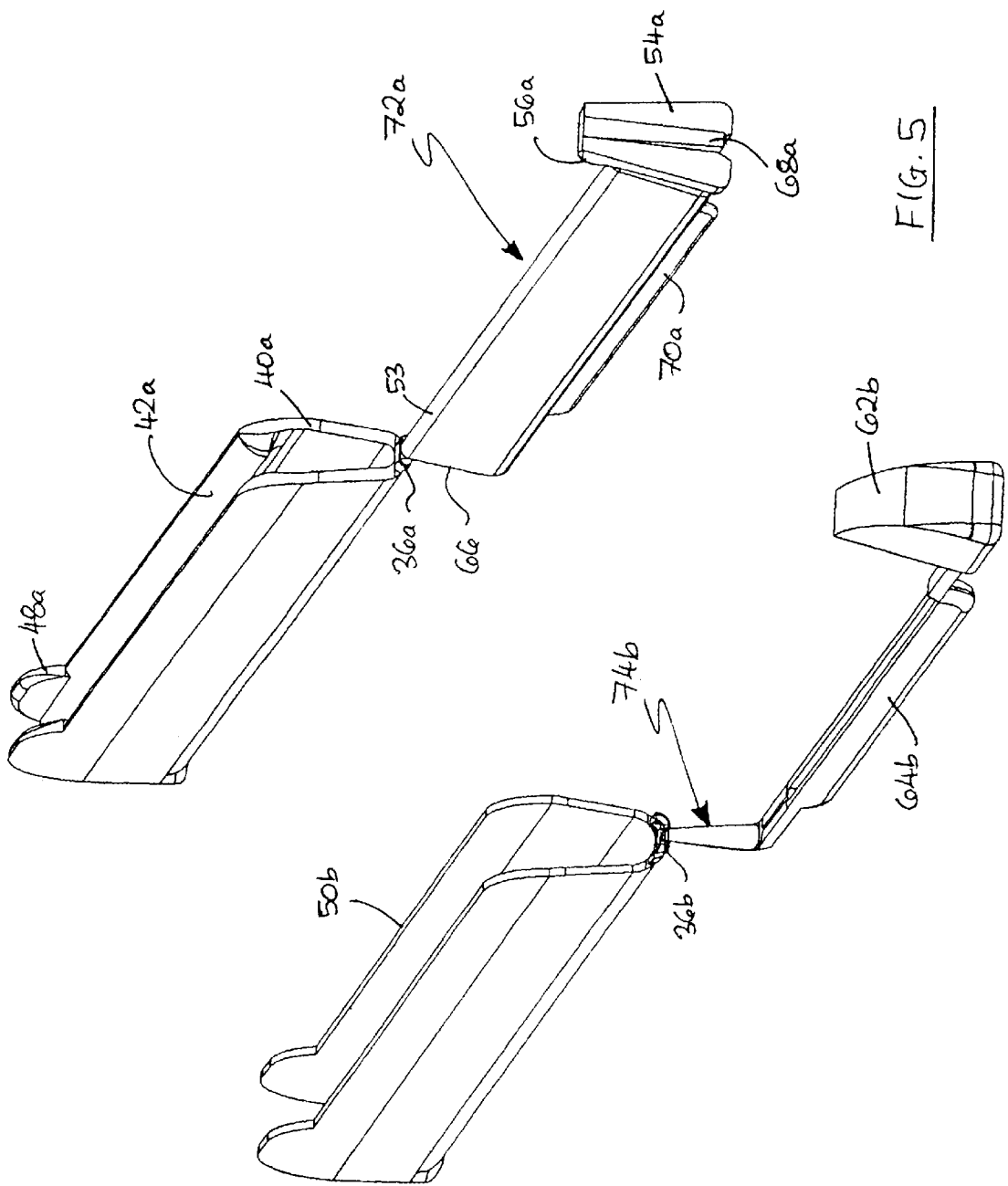
FIG. 5 is a schematic exploded view showing the shapes of the first and second shots of molding.

Referring to FIGS. 2, 3 and 5, the trough member 34 comprises an inner channel 40a of the first (hard) plastics. The inner channel 40a includes longitudinal, confronting lips 42a defining a constriction at the channel mouth. Each lip 42a has an upper tapered surface 44 and a lower abutment surface 46 which is more abrupt than the tapered surface 44. The lips 42a run substantially the entire length of the trough member 34. The sides of the inner channel 40a diverge slightly to give the channel a slight wedge shape. At the distal end of the inner channel 40a, finger tabs 48a extend upwardly from the channel mouth, such that the tabs 48a also diverge slightly. The inner channel 40a is covered by an outer skin 50b of the second plastics. The skin 50b covers at least the majority of the exterior surface, and in this embodiment, substantially all of the exterior surface, including the outer faces of the finger tabs 48.

Referring to FIGS. 2, 4 and 5, the blade member 32 comprises a wedge member 52a of the first plastics, and having a tapered nose 53. The wedge member 52a is dimensioned to fit within the inner channel 40a when the clamp 30 is closed. The inner channel 40a deforms sufficiently to allow the wedge member 52a to pass over the lips 42a, and to locate behind the lips 42a when in the closed position. At its distal end, the wedge member 52a comprises flange 54a which carries a locking projection 56a. The locking projection is dimensioned to locate behind a distal edge 58a of the inner channel 40a (FIGS. 2, 6 and 7) near the bottom or floor of the inner channel 40a when the clamp 30 is in its closed position.

In a similar manner to the trough member 34, the blade member 32 also comprises an outer portion 60b of the second plastics. The outer portion 60b includes a finger handle 62b as an extension of the flange 54a, the two together forming the handle 38 mentioned above. The outer portion 60b further includes a back or spine portion 64b which runs along the edge of the wedge member 52a opposite to the tapered nose 53, and along the proximal end face 66 of the wedge member 52a to the hinge strap 36. In contrast to the trough member 34 (which provides large areas of contact between the portions of the first and second plastics), the amount of contact area between the portions of first and second plastics in the blade member 32 is relatively small. Therefore, mechanical keying can be used to assist in establishing firm attachment between the first and second plastics. The mechanical keying is provided by a rib 68a projecting from the flange (FIG. 5), and a longitudinal fin 70a projecting from the back of the wedge member 52a opposite to the tapered nose 53.

The bond between the first and second materials can also be molecular, depending on the choice of materials used. This type of bond is enhanced by maximizing the surface area of interface between the first and second materials. The strength of the bond is generally proportional to the surface area of the interface.

As best seen in FIG. 5, in the this embodiment, the inner channel 40a and the wedge member 52a are joined at the hinge strap as a single continuous molding 72a of the first plastics material. Similarly, the skin 50b and the outer portion 60b are joined at the hinge strap as a single continuous molding 74b of the second plastics material. This provides advantages in terms of molding, since only a single mould gate or injection port is required for molding each portion 72a and 74b.

In use, once the clamp 30 has been closed one or more times, it is possible that one of the plastics will break at the hinge strap 36 (as seen for example in FIG. 6). This is because the clamp is molded in an open condition, and the outermost layer of the strap will inevitably be stretched when the clamp is moved to its closed position. In the present embodiment, the soft plastics will be stretched, and so is likely to break. However, such breakage of the soft material at the hinge does riot weaken the hinge strap.

In this embodiment, a two-shot molding process is used to form the clamp. Preferably, the first portion 72a is molded first, after which the second portion 74b is molded as a skin or "over-mold" on the first molding 72a. This order is preferred, as it allows the mould tool to be simplified by molding the inner portion 72a first. However, it will be appreciated that the order of the moldings may be reversed if desired. Two-shot (or multi-shot) molding is a known technique in which two different plastics are molded one after the other, the two plastics bonding to each other at their regions of mutual contact. For two-shot molding, the first and second plastics should preferably be selected to be compatible with each other to form a reliable bond. If non-compatible materials are used, then either mechanical keying, or an intermediate bond layer, may be required to provide secure attachment of one plastics to the other.

In use, the inner channel 40a and the wedge member 52a of the first (hard) plastics provide the clamp 30 with the necessary structural rigidity to ensure reliable clamping action effective to close an outlet of an ostomy pouch. The skin 50b and the outer portion 60b provide an exterior surface which has a soft or cushioned feel, to provide more comfort for the user. The integral molding of the first and second plastics therefore enables the clamp 30 to be designed with the comfort of the user in mind, without detracting from the clamping properties needed for reliable use.

In order to close the clamp 30, the clamp 30 is placed with its blade member 32 and trough member 34 on either side of an ostomy pouch outlet to be closed, and the blade member 32 is pivoted closed into the trough member 34. As explained above, there are two inter-engaging profiles on the blade member 32 and the trough member 34 which lock the clamp 30 in its closed position, and which create the seal of the pouch outlet. The first is the engagement between the locking projection 56a and the distal edge 58a of the floor of the inner channel 40a. In this embodiment, this represents the primary latch for the clamp. The hinge strap 36 allows a small degree of longitudinal movement of the blade member 32 relative to the trough member 34, sufficient to allow the locking projection 56a to snap over the distal edge 58a of the inner channel 40a to lock the two closed, since the locking projection 56a is immovable relative to the remainder of the blade member. The second is the engagement between the longitudinal lips 42a and the rear edge of the wedge member 52a. As the blade member 32 approaches its fully closed position, the sides of the inner channel 40a deform outwardly to allow the wedge member 52a to ramp over the tapered surfaces 44 of the lips 42a, and to snap into position to be locked by the lower abutment surfaces 46 of the lips 42a.

Figure 1:
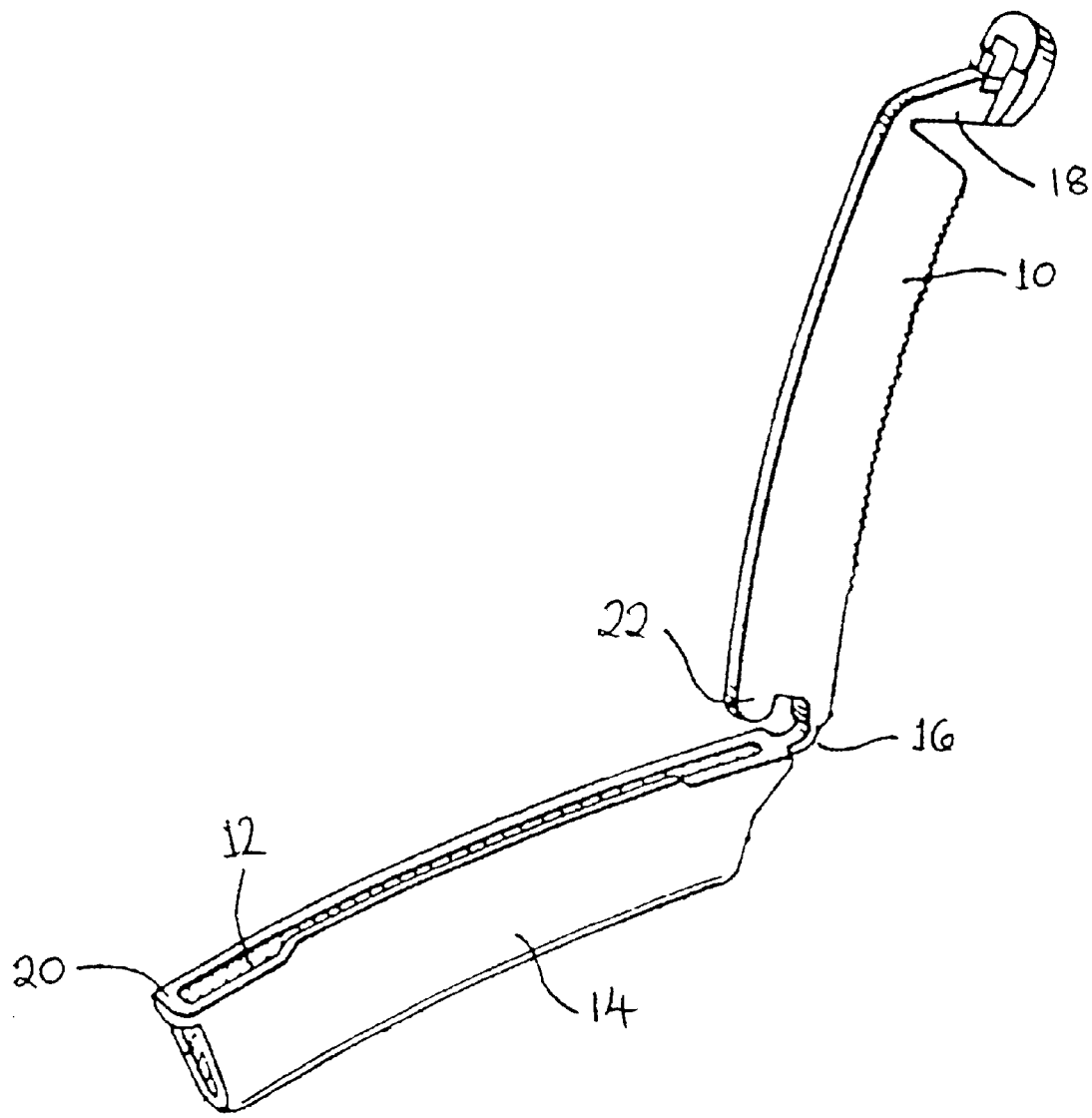
FIG. 1 is a schematic perspective view of a conventional ostomy pouch clamp.

Therefore, in its closed position, the clamp 30 is retained closed by a combination of the locking projection 56a at the distal end of the clamp, the hinge strap 36 at the proximal end of the clamp, and the lips 42a along substantially the entire length of the clamp. This provides an optimum mechanical engagement along the entire length of the clamp 30, rather than merely at the ends, as in the conventional arrangement of FIG. 1. Even if one of the above three engagements should fail, for example, if the hinge strap 36 should break, then the other engagements, particularly that provided by the lips 42a, are sufficient to lock the clamp shut securely.

Figure 8:
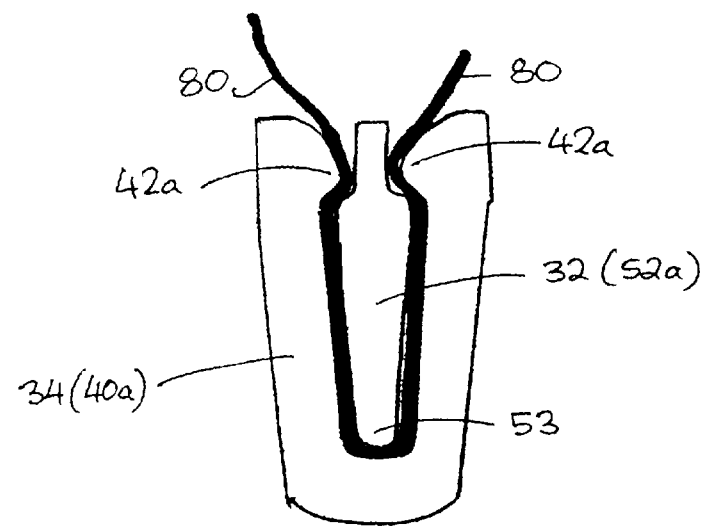
FIG. 8 is an enlarged schematic section showing the clamp in its closed position clamping an ostomy pouch outlet.

As best seen in FIG. 8, in the closed position of the clamp, the ostomy pouch outlet (denoted by numeral 80) is folded around the nose 53 of the wedge member 52a, and is trapped tightly between the wedge member 52a and the inner channel 40a. In this embodiment, the wedge member 52a and the inner channel 40a are both made of the first, relatively hard, plastics to provide relatively unyielding surfaces for directly clamping the ostomy pouch outlet 80. Additionally, at the upper end of the clamp 30, the pouch outlet is folded tightly around the lips 42a of the inner channel 40a. This extends the clamping region of the clamp 30 compared to the conventional clamp of FIG. 1, and also causes the pouch outlet to be folded along a more tortuous path, thereby reducing the chance of leakage through the outlet 80.

In order to open the clamp 30, the user applies finger pressure to the handle 38 and to the finger tabs 48 in the direction shown by arrows 82 in FIG. 7. The finger pressure is sufficient to overcome the interference lock between the locking projection 56a of the blade member 32 and the distal edge 58a of the inner channel 40a. It is also sufficient to spread the finger tabs 48 slightly, and to open the channel mouth to allow the blade member 32 to separate from the trough member 34. Therefore, this embodiment can enable the clamp to be opened more easily and intuitively than a conventional clamp using a cantilever lock.

In the above embodiment, both the blade member 32 and the trough member 34 are made of first and second different plastics. However, it will be appreciated that if desired, the two plastics could be limited to only one member, with the other member being made of only one type of plastics. For example, in a modified embodiment, the trough member may be made of the two plastics (with a soft outer skin), and the blade member made of only a single plastics. This would still provide a substantial exterior surface covered by the soft skin, to provide a comfortable feel for the user.

It will be appreciated that the foregoing description is merely illustrative of a preferred form of the invention, and that many modifications and improvements may be made without departing from the principles and/or scope of the invention. Accordingly, the claims are intended to be broadly construed to cover all such improvements and modifications.

What is claimed is:

1. A closure for closing an outlet of an ostomy pouch, the closure comprising:
    a blade member; and
    a trough member hingedly coupled to the blade member and having a channel for receiving at least a portion of the blade member;
    wherein at least one of the blade member and the trough member comprises a first portion of a first relatively hard plastics, and a second portion of a second relatively deformable plastics, the first and second portions being integrally molded.

2. A closure according to claim 1, wherein the blade member and the trough member are integrally molded, and are joined by an integral hinge.

3. A closure according to claim 1, wherein said first portion comprises a closureing surface of said closure.

4. A closure according to claim 1, wherein said second portion comprises an external surface of said closure.

5. A closure according to claim 1, wherein the trough member comprises said first portion as a channel member for receiving said blade member, and said second portion as a cover at least partially covering an external surface of said channel member.

6. A closure according to claim 5, wherein said cover covers at least a majority of the exterior surface of said channel member.

7. A closure according to claim 5, wherein said cover covers substantially the side surfaces of said channel member.

8. A closure according to claim 5, wherein said cover covers substantially the entire external surface of said channel member.

9. A closure according to claim 5, wherein said channel member comprises at least one inwardly facing projection for forming a channel constriction towards an open mouth of the channel.

10. A closure according to claim 1, wherein said blade member comprises said first portion as a elongate portion of said blade member to be received by said trough member, and said second portion as an external portion of said blade member which is located at least partly outside said channel when said elongate portion is received in said trough member.

11. A closure according to claim 10, wherein said first portion comprises a locking projection for forming locking engagement with said trough member when said elongate portion is received in said trough member.

12. A closure according to claim 11, wherein said locking projection is located to cooperate with a distal end of said trough member adjacent to a bottom of the channel.

13. A closure according to claim 11, wherein each of said blade member and said trough member comprises a said first portion and a said second portion.

14. A closure for closing an outlet of an ostomy pouch, the closure comprising:
    a blade member comprising a first portion of a first relatively hard plastics, and a second portion of a second relatively deformable plastics, the first and second portions being integrally molded; and
    a trough member hingedly coupled to the blade member and having a channel for receiving at least a portion of the blade member, the trough member comprising a third portion of said first relatively hard plastics, and a fourth portion of said second relatively deformable plastics, said third and fourth portions being integrally molded.

15. A closure according to claim 14, wherein said first and third portions form a continuous molding.

16. A closure according to claim 14, wherein said second and fourth portions form a continuous molding.

17. A closure according to claim 14, wherein said first and third portions are joined at a hinge.

18. A closure according to claim 14, wherein said second and fourth portions are joined at a hinge.

* * * * *